(12) United States Patent
Myyrylainen et al.

(10) Patent No.: US 10,667,770 B2
(45) Date of Patent: Jun. 2, 2020

(54) INTRA-ORAL IMAGING

(71) Applicant: Nokia Technologies Oy, Espoo (FI)

(72) Inventors: Lea Myyrylainen, Espoo (FI); Katri Helena Pohjonen, Espoo (FI)

(73) Assignee: Nokia Technologies Oy, Espoo (FI)

( * ) Notice: Subject to any disclaimer, the term of this patent is extended or adjusted under 35 U.S.C. 154(b) by 82 days.

(21) Appl. No.: 15/426,264

(22) Filed: Feb. 7, 2017

(65) Prior Publication Data

US 2017/0224293 A1 Aug. 10, 2017

(30) Foreign Application Priority Data

Feb. 10, 2016 (EP) ..................... 16154968

(51) Int. Cl.
| | |
|---|---|
| *A61B 6/14* | (2006.01) |
| *A61B 6/00* | (2006.01) |
| *A61B 1/04* | (2006.01) |
| *A61B 1/06* | (2006.01) |
| *A61B 1/24* | (2006.01) |
| *A61B 5/00* | (2006.01) |
| *A61C 9/00* | (2006.01) |
| *G01T 1/16* | (2006.01) |
| *G01T 1/20* | (2006.01) |

(52) U.S. Cl.
CPC ............ *A61B 6/145* (2013.01); *A61B 1/04* (2013.01); *A61B 1/0661* (2013.01); *A61B 1/24* (2013.01); *A61B 5/0086* (2013.01); *A61B 5/0088* (2013.01); *A61B 6/425* (2013.01); *A61B 6/4216* (2013.01); *A61B 6/4417* (2013.01); *A61B 6/482* (2013.01); *A61C 9/008* (2013.01); *G01T 1/1603* (2013.01); *G01T 1/2018* (2013.01)

(58) Field of Classification Search
None
See application file for complete search history.

(56) References Cited

U.S. PATENT DOCUMENTS

| | | |
|---|---|---|
| 6,256,524 B1 | 7/2001 | Walker et al. |
| 7,563,026 B2 | 7/2009 | Mandelkam et al. |
| 7,613,505 B2 | 11/2009 | Mazuir et al. |
| 8,002,465 B2 | 8/2011 | Ahn |

(Continued)

FOREIGN PATENT DOCUMENTS

| | | |
|---|---|---|
| CN | 1493253 A | 5/2004 |
| CN | 102300979 A | 11/2011 |

(Continued)

OTHER PUBLICATIONS

Hatzistratis et al., "Hybrid Pixel Detectors for Gamma/X-Ray Imaging", Journal of Physics: Conference Series, vol. 637, 2015, pp. 1-4.

(Continued)

*Primary Examiner* — Hoon K Song
(74) *Attorney, Agent, or Firm* — Alston & Bird LLP

(57) ABSTRACT

An probe body comprising:
one or more light sources; one or more light sensors; an x-ray detector configured to detect, using at least one of the one or more light sensors, light from a scintillator for converting extra-orally applied x-rays to light; and a lower energy light detector configured to detect, using at least one of the one or more light sensors, light from an object illuminated by at least one of the one or more light sources.

19 Claims, 3 Drawing Sheets

(56) References Cited

U.S. PATENT DOCUMENTS

| | | | |
|---|---|---|---|
| 8,898,069 B2 | 11/2014 | Hood et al. | |
| 2003/0169847 A1* | 9/2003 | Karellas | A61B 6/481 378/98.3 |
| 2004/0258210 A1* | 12/2004 | Ritter | A61B 5/0064 378/198 |
| 2005/0226390 A1* | 10/2005 | Ihalainen | A61B 6/14 378/191 |
| 2006/0067462 A1 | 3/2006 | Hack | |
| 2007/0106138 A1 | 5/2007 | Beiski et al. | |
| 2008/0279330 A1* | 11/2008 | Ueki | A61B 5/0091 378/63 |
| 2009/0047691 A1 | 2/2009 | Huwig et al. | |
| 2010/0152599 A1 | 6/2010 | DuHamel et al. | |
| 2010/0291665 A1 | 11/2010 | Margraf et al. | |
| 2011/0051903 A1 | 3/2011 | Armencha et al. | |
| 2011/0054938 A1 | 3/2011 | Hood et al. | |
| 2013/0253286 A1 | 9/2013 | Fridman | |
| 2014/0212840 A1 | 7/2014 | Nguyen et al. | |
| 2014/0272764 A1 | 9/2014 | Miller et al. | |
| 2015/0250433 A1 | 9/2015 | Hyde et al. | |
| 2016/0367188 A1 | 12/2016 | Malik et al. | |
| 2017/0202526 A1 | 7/2017 | Palermo | |
| 2017/0319054 A1* | 11/2017 | Miller | A61B 1/0684 |

FOREIGN PATENT DOCUMENTS

| | | |
|---|---|---|
| CN | 102711588 A | 10/2012 |
| CN | 104207800 A | 12/2014 |
| CN | 204698735 U | 10/2015 |
| EP | 1477116 A1 | 11/2004 |
| EP | 2392260 A2 | 12/2011 |

OTHER PUBLICATIONS

"Seeing the Light: Innovative Intraoral Imaging Technologies", Dental Economics, Retrieved on Mar. 21, 2017, Webpage available at: http://www.dentaleconomics.com/articles/print/volume-105/issue-2/science-tech/seeing-the-light-innovative-intraoral-imaging-technologies.html.

"Soprolife The Blue Revolution", Acteon, Retrieved on Mar. 21, 2017, Webpage available at: https://www.acteongroup.com/en/my-products/imaging/diagnostic-camera/soprolife.

"ScanX DR X-ray Sensor", Allpro Imaging, Retrieved on Mar. 21, 2017, Webpage available at: http://allpro-imaging.com/vet/scanx-dr-dental-x-ray-sensor-vet.html.

Simon et al., "Transillumination and Reflectance Probes for In Vivo Near-IR Imaging of Dental Caries", Proc SPIE Int Soc Opt Eng, vol. 8929, Feb. 18, 2014, pp. 1-16.

"Easy Go CMOS Wireless Intra Oral Camera", Made-in-china.com, Retrieved on Mar. 21, 2017, Webpage available at: http://huaer-technology.en.made-in-china.com/product/mvzxSktlOEVB/China-Easy-Go-CMOS-Wireless-Intra-Oral-Camera.html.

"Intraoral Camera & Dental Camera", KAVO Dental Excellence, Retrieved on Mar. 21, 2017, Webpage available at: http://www.kavo.com/en/dental-x-ray-machines-and-diagnostics/intraoral-camera-dental-camera.

"Treatment Planning", Sirona The Dental Company, Retrieved on Mar. 21, 2017, Webpage available at: http://www.sirona.com/en/products/imaging-systems/treatment-planning/?tab=3694.

Extended European Search Report received for corresponding European Patent Application No. 16154968.8, dated Aug. 24, 2016, 4 pages.

Extended European Search Report received for corresponding European Patent Application No. 16157078.3, dated Jun. 20, 2016, 6 pages.

Malon et al_, "Saliva-Based Biosensors: Noninvasive Monitoring Tool for Clinical Diagnostics", Hindawi BioMed Research International, vol. 2014, 2014, 21 Pages.

Kim et al., "Non-invasive mouthguard biosensor for continuous salivary monitoring of metabolites", The Analyst, vol. 139, No. 7, 2014, pp. 1632-1636.

Office Action received for corresponding European Patent Application No. 16157078.3, dated Aug. 8, 2018, 4 pages.

Office Action for U.S. Appl. No. 15/437,313, dated Dec. 14, 2018, 18 pages.

Office Action for U.S. Appl. No. 15/437,313, dated May 2, 2019, 17 pages.

Advisory Action for U.S. Appl. No. 15/437,313 dated Jul. 18, 2019.

Notice of Allowance for U.S. Appl. No. 15/437,313 dated Dec. 27, 2019.

Office Action for U.S. Appl. No. 15/437,313 dated Dec. 14, 2018.

Office Action for U.S. Appl. No. 14/437,313 dated May 2, 2019.

Anastasiou, A. et al., *Biomedical Impact In Implantable Devices—The Transcatheter Aortic Valve As An Example*, BIOMEP 2015, Journal of Physics: Conference Services 637 (2015) 4 pages.

Child, P. L., Jr., *Digital Dentistry: Is This The Future of Dentistry*, Dental Economics [online] [retrieved Feb. 4, 2020]. Retrieved via the Internet: https://www.dentaleconomics.com/science-tech/article/16394539/digital-dentistry-is-the-the . . . (Oct. 2011) 13 pages.

CR Systems For Veterinairans // Digital imaging // ALLPRO Imaging [online] [retrieved Feb. 4, 2020]. Retrieved via the Internet: https://web.archive.org/web/20150826083648/http://allpro-imaging.com/vet/ (Aug. 26, 2015) 3 pages.

Dental Imaging and Diagnosis Tool | SOPROLIFE [online] [retrieved Feb. 4, 2020]. Retrieved via the Internet: https://web.archive.org/web/20161102030130/http://www.soprolife.com/ (Nov. 2, 1016) 1 page.

Clinical Articles of Dental Imaging by Fluorescence | SOPROLIFE [retrieved Feb. 4, 2020]. Retrieved via the Internet: https://web.archive.org/web/20160128105742/http://www.soprolife.com/fluorescence-imaging/clinical-articles.php (Oct. 28,2016) 2 pages.

Blog by ClearDent Dental Software:Software is Key to a Good Digital X-ray [online] [retrieved Feb. 4, 2020]. Retrieved via the Internet: https://web.archive.org/web/20130114071857/http://news.cleardent.com/2013/01/software-is-key-to-good-digital-x-ray.html (Jan. 14, 2013) 5 pages.

Office Action for Chinese Application No. 2017101009878 dated Nov. 12, 2019, 12 pages.

\* cited by examiner

INTRA-ORAL IMAGING

TECHNOLOGICAL FIELD

Embodiments of the present invention relate to industrial and medical imaging and, in particular, intra-oral imaging

BACKGROUND

Intra-oral imagery may be used to image the bones, teeth and soft tissues with the oral cavity of a human or animal.

Such imagery may be used to identify problems or potential problems such as tooth decay, infection, cancer etc.

BRIEF SUMMARY

According to various, but not necessarily all, embodiments of the invention there is provided probe body comprising: one or more light sources; one or more light sensors; an x-ray detector configured to detect, using at least one of the one or more light sensors, light from a scintillator for converting extra-orally applied x-rays to light; and a lower energy light detector configured to detect, using at least one of the one or more light sensors, light from an object illuminated by at least one of the one or more light sources.

The probe may be an intra-oral probe or another type of probe. The object may be a tooth.

According to various, but not necessarily all, embodiments of the invention there is provided an intra-oral probe body comprising: one or more light sources; one or more light sensors; an x-ray detector configured to detect, using at least one of the one or more light sensors, light from a scintillator for converting extra-orally applied x-rays to light; and a lower energy light detector configured to detect, using at least one of the one or more light sensors, light from a tooth illuminated by at least one of the one or more light sources.

The combination of two detectors (an x-ray detector and a lower energy light detector) within a single probe improves intra-oral imaging. It is cheaper and more convenient to capture images using different imaging techniques. It is easier to obtain images using different imaging techniques and to use differential analysis comparing the images. It is more accurate to combine images from the two detectors.

According to various, but not necessarily all, embodiments of the invention there is provided an intra-oral probe body for a hybrid imaging system comprising: one or more light sources; one or more light sensors; an x-ray detector configured to detect, using at least one of the one or more light sensors, light from a scintillator for converting extra-orally applied x-rays to light; and a lower energy light detector configured to detect, using at least one of the one or more light sensors, light from a tooth illuminated by at least one of the one or more light sources.

According to various, but not necessarily all, embodiments of the invention there is provided an intra-oral probe body comprising: a lower energy light detector comprising one or more light sources and one or more first light sensors configured to detect light from a tooth illuminated by the one or more light sources; and an x-ray detector comprising one or more second light sensors configured to detect light from a scintillator for converting extra-orally applied x-rays to light.

According to various, but not necessarily all, embodiments of the invention there is provided a method of hybrid imaging comprising: using a single intra-oral probe body 110 for x-ray imaging and lower energy light imaging.

According to various, but not necessarily all, embodiments of the invention there is provided examples as claimed in the appended claims.

BRIEF DESCRIPTION

For a better understanding of various examples that are useful for understanding the brief description, reference will now be made by way of example only to the accompanying drawings in which.

DETAILED DESCRIPTION

Figure 1:
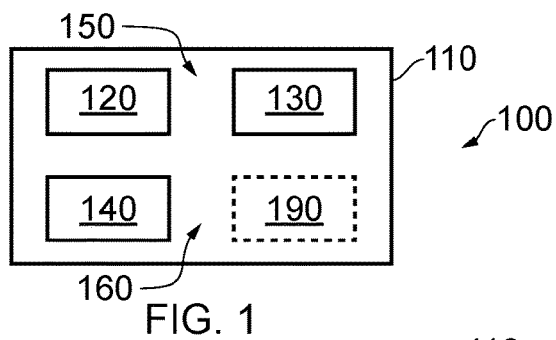
FIG. 1 illustrates an example of a hybrid imaging system.

The figures illustrate various examples of a hybrid imaging system 100 comprising: an intra-oral probe body 110 comprising: one or more light sources 120; one or more light sensors 130; an x-ray detector 160 configured to detect, using at least one of the one or more light sensors 130, light from a scintillator 140 for converting extra-orally applied x-rays to light; and a lower energy light detector 150 configured to detect, using at least one of the one or more light sensors 130, light from a tooth illuminated by at least one of the one or more light sources 120.

The x-ray detector 160 and the lower energy light detector 150 may be configured to image the same tooth or different teeth using the one or more light sensors 130. They may, for example, be used to image the same portion of a tooth, or different portions or surfaces of the same tooth.

In some but not necessarily all examples, where the x-ray detector 160 and the lower energy light detector 150 are configured to image the same portion of a tooth, light sensors 130 used by the x-ray detector 160 for x-ray imaging may also be used, at a different time, by the lower energy light detector 150 for lower energy light imaging. In this example the scintillator 140 used by the x-ray detector 160 may be detachable.

In some but not necessarily all examples, where the x-ray detector 160 and the lower energy light detector 150 are configured to image a different tooth or different portions or surfaces of the same tooth, the light sensors 130 used by the lower energy light detector 150 for lower energy light imaging (first light sensors 132) are not used by the x-ray detector 160 for x-ray imaging and the light sensors 130 used by the x-ray detector 160 for x-ray imaging (second light sensors 134) are not used by the lower energy light detector 150 for lower energy light imaging.

The x-ray detector 160 and the lower energy light detector 150 may be configured to image the same tooth using different light sensors 130 at the same time.

The intra-oral probe body 110 may be configured to flex and/or be configured to bend and/or be configured to contort. This may allow the intra-oral probe body 110 to conform to the intra-oral anatomy of a human or animal This may also enable the first light sensors 132 of the lower energy light detector 150 to be used for imaging one surface of a tooth and for the second light sensors 134 of the x-ray detector 160 to be used for imaging through a different, surface of the tooth.

The term 'flex' implies that the intra-oral probe body 110 is pliable and can be acted upon by a user to change its shape. A flexible intra-oral probe body 110 may be stably flexible (retains a new shape) or resiliently flexible (returns to a default shape). The term 'bend' implies that the intra-oral probe body 110 is configured to change its shape so that it has a distinct deviation from straight at a curved bend or angular bend. The term 'contort' implies that the intra-oral probe body 110 is configured to change its shape so that it is twisted, drawn or bent out of shape.

Advantages that may be provided by examples of the invention include:
simultaneous imaging of the same object using the x-ray detector 160 and the lower energy light detector 150;
improved synchronisation between images captured using the x-ray detector 160 and the lower energy light detector 150;
an increased precision in imaging helping to increase diagnostic accuracy;
precise monitoring of interventional procedures;
potentially reducing the number of x-ray exposures required;
an increased efficiency in time for both patients and practitioners;
enabling the use of common electronics (including display and user interface) and software (including imaging algorithms) for both the x-ray detector 160 and the lower energy light detector 150 reducing cost or improving quality.

Referring now to each of the illustrated examples, FIG. 1 illustrates an example of a hybrid imaging system 100.

The hybrid imaging system 100 comprises: an intra-oral probe body 110 that may be positioned inside the oral cavity of an animal or human Where the hybrid imaging system 100 is used for in vivo imaging, the intra-oral probe body 110 will be formed from material that is non-toxic to the subject.

The intra-oral probe body 110 is configured so that single probe may be used for both x-ray imaging (radiography) and lower energy light imaging.

Lower energy light imaging involves the illumination of a target with light that has a lower energy than the x-ray portion of the electromagnetic spectrum and the detection of light that has a lower energy than the x-ray portion of the electromagnetic spectrum. In lower energy light imaging, the light used for illumination may have the same energy as the light detected or the light used for illumination may have a higher energy than the light detected. The light used for illumination and the light detected may be, for example, non-ionizing electromagnetic radiation.

The light used for illumination and the light detected may be, for example, ultraviolet light (e.g. wavelength 200-400 nm) near ultraviolet light (e.g. wavelength 300-400 nm), visible light (e.g. wavelength 380-760 nm), near infra red light (e.g. wavelength 750-2500 nm) or infrared light (e.g. wavelength 750 nm-1 mm) or any combination of these. The light used for illumination may be, for example, light at any wavelengths between ultraviolet and infrared (e.g. wavelength 200 nm-1 mm) or between near ultraviolet and near infrared (e.g. wavelength 300 nm-2500 nm). The light detected may be, for example, light at any wavelengths between ultraviolet and infrared (e.g. wavelength 200 nm-1 mm) or between near ultraviolet and near infrared (e.g. wavelength 300 nm-2500 nm).

X-ray imaging involves passing x-rays through a target. Typically the x-rays after passing through the target are converted to lower energy photons using a scintillator 140 and the lower energy photons are detected. The x-rays are generated and applied from outside the oral cavity (extra-orally).

In some examples, the same light sensors 130 may be used for detection of lower energy photons for x-ray imaging and for lower energy light imaging. In other examples, different light sensors 130 may be used for detection of lower energy photons for x-ray imaging and for lower energy light imaging.

The intra-oral probe body 110 comprises: one or more light sources 120; one or more light sensors 130; an x-ray detector 160 configured to detect, using at least one of the one or more light sensors 130, light from a scintillator 140 for converting extra-orally applied x-rays to light; and a lower energy light detector 150 configured to detect, using at least one of the one or more light sensors 130, light from a tooth illuminated by at least one of the one or more light sources 120.

Figure 2:
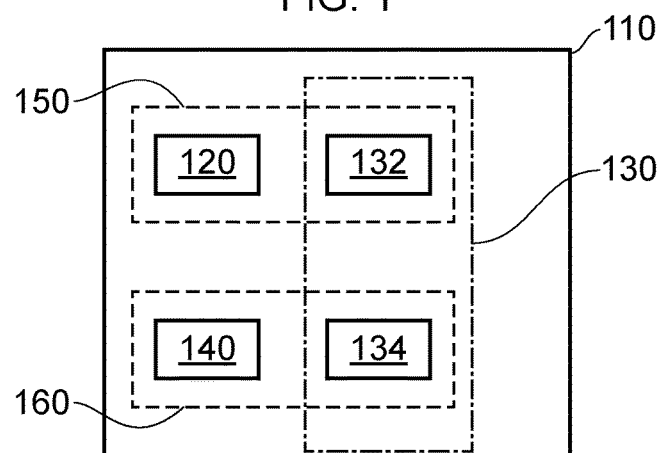
FIG. 2 illustrates an example of the hybrid imaging system illustrated in FIG. 1.

FIG. 2 illustrates an example of the hybrid imaging system 100 illustrated in FIG. 1.

In this example, the one or more light sensors 130 comprises one or more first light sensors 132 and one or more different second light sensors 134. The lower energy light detector 150 is configured to detect, using the one or more first light sensors 132, light from a tooth 200 illuminated by at least one of the one or more light sources 120. The x-ray detector 160 is configured to detect, using at least one of the one or more second light sensors 134, light from a scintillator 140 for converting extra-orally applied x-rays to light.

The hybrid imaging system 100 therefore comprises: an intra-oral probe body 110 comprising: a lower energy light detector 150 comprising one or more light sources 120 and one or more first light sensors 132 configured to detect light from a tooth illuminated by the one or more light sources 120; and an x-ray detector 160 comprising one or more second light sensors 134 configured to detect light from a scintillator 140 for converting extra-orally applied x-rays to light.

Figure 3:
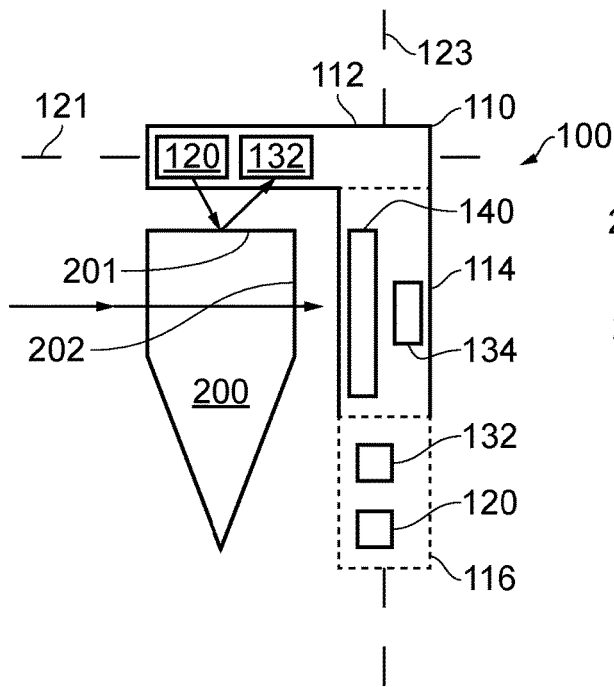
FIGS. 3 and 4 illustrate an example or examples of the hybrid imaging system illustrated in FIG. 2.
Figure 4:
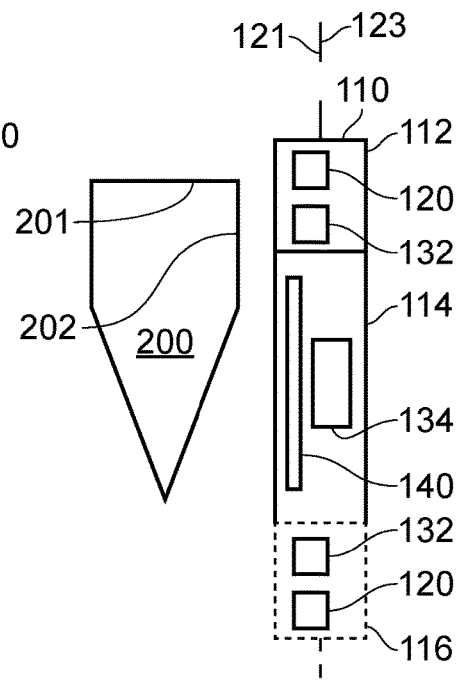

As illustrated in FIGS. 3 and 4, the scintillator 140 is positioned to an anterior side of the one or more second light sensors 134 on a posterior side 202 of a tooth 200. The scintillator 140 is positioned between the tooth 200 and the one or more second light sensors 134. The scintillator 140 is also positioned not to obstruct light from a tooth 200, illuminated by at least one of the one or more light sources 120, from travelling to the one or more first light sensors 132.

The intra-oral probe body 110 in some but not necessarily all examples comprises at least a first part 112 and a second part 114. The first part 112 houses the lower energy light detector 150 comprising the one or more first light sensors 132 and the one or more light sources 120 and the second part 114 houses the x-ray detector 160 comprising a scintillator 140 and the one or more second light sensors 134.

In FIG. 3, the first part 112 is adjacent a top surface 201 of a tooth 200 and the second part 114 is adjacent a posterior surface 202 of the same tooth 200 but not the top surface 201 of the tooth 200. In the illustrated example, the one or more first light sensors 132 and the one or more light sources 120 of the first part 112 lie substantially in a first plane 121 and the one or more second light sensors 134 of the second part 114 lie substantially in a second plane 123 that is orthogonal to the first plane.

In FIG. 4, the first part 112 is adjacent a posterior surface 202 of a tooth 200 and the second part 114 is adjacent the posterior surface 202 of the same tooth 200 (or a different tooth). In the illustrated example the first part 112 and the second part 114 are adjacent a posterior surface 202 of the same tooth 200, because the first part 112 and the second part 114 are vertically aligned. However, in other examples the intra-oral probe body 110 may rotated 90 degrees so that the first part 112 and the second part 114 are horizontally aligned and the first part 112 and the second part 114 are adjacent posterior surfaces 202 of different teeth 200.

In the illustrated example of FIG. 4, the one or more first light sensors 132 and the one or more light sources 120 of the first part 112 lie substantially in a first plane 121 and the one or more second light sensors 134 of the second part 114 lie substantially in a second plane 123 that is parallel to the first plane 121.

In some but not necessarily all examples, the first part 112 and the second part 114 have a fixed configuration and are not movable relative to each other.

In other examples, the first part 112 and the second part 114 have a variable configuration and are movable relative to each other. For example, the first part 112 may be movable relative to the second part 114 between at least a first configuration, as illustrated in FIG. 3, and a second configuration, as illustrated in FIG. 4.

Referring back to FIG. 1, the intra-oral probe body 110 may comprise a detector 190 configured to detect a change in configuration of the intra-oral probe body 110 and configured to produce, in response to a change in the configuration of the intra-oral probe body 110, an electronic change of configuration signal. This signal may be used to change a state of electronic circuitry of the hybrid imaging system 100 or to indicate a change in an imaging plane of the lower energy light detector 150 relative to an imaging plane of the x-ray detector 160 so that the different orientation of the imaging planes may be taken into account when producing a composite image by combining an image captured by the lower energy light detector 150 and an image captured by the x-ray detector 160. An example of a detector 190 is a strain gauge.

Also illustrated as an optional feature in FIGS. 3 and 4, using dashed lines, is that the intra-oral probe body 110 comprises a third part 116, wherein the third part 116 houses a further lower energy light detector 150 comprising one or more light sensors 130 and one or more light sources 120. The second part 114 lies between the first part 112 and the third part 116. The features described above in relation to the first part 112 are also applicable to the third part 116. The first part 112 and the third part 116 may be used simultaneously. The first part 112 may be used to image an upper jaw or one or more teeth of the upper jaw and the third part 116 may be used to image a lower jaw or one or more teeth of the lower jaw. The first part 112 and/or the third part 116 may be bent relative to the second part 114 as illustrated in FIG. 3.

Figure 5A:
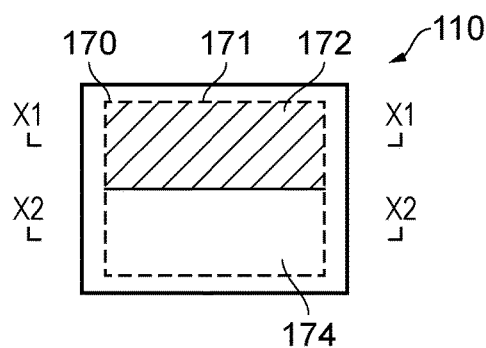
FIG. 5A illustrates a plan view of an example of an intra-oral probe body as illustrated in FIGS. 2, 3 and 4
Figure 5B:
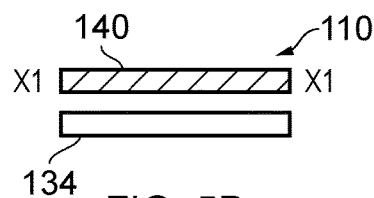
FIG. 5B illustrates a cross-section of the intra-oral probe body illustrated in FIG. 5A through the x-ray detector and FIG. 5C illustrates a cross-section of the intra-oral probe body illustrated in FIG. 5A through the lower energy light detector.
Figure 5C:
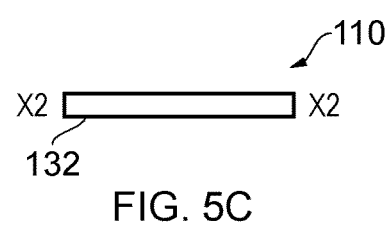

FIG. 5A illustrate a plan view of an example of an intra-oral probe body 110 as illustrated in FIGS. 2, 3 and 4. FIG. 5B illustrates a cross-section of the intra-oral probe body 110 illustrated in FIG. 5A through the x-ray detector 160. FIG. 5C illustrates a cross-section of the intra-oral probe body 110 illustrated in FIG. 5A through the lower energy light detector 150.

In this example, the second light sensors 134 are arranged to sense within a first sub-area 172 of a first area 170 and the first light sensors 132 are arranged to sense within a second sub-area 174 of the first area 170, The first sub-area 172 and the second sub-area 174 do not overlap.

The scintillator 140 is positioned within a perimeter 171 of the first area 170 and overlies the first sub-area 172 but not the second sub-area 174.

In some but not necessarily all examples, the light sources 120 may be arranged around a perimeter 171 of the first area 170 or around a perimeter of the second sub-area 174.

Figure 6A:
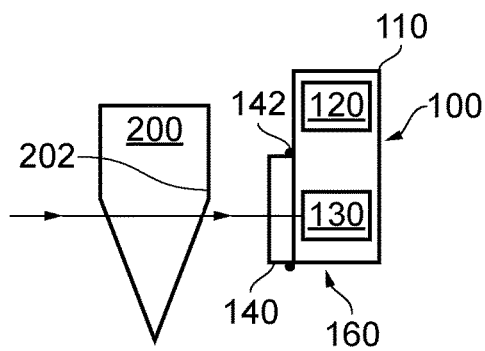
FIGS. 6A and 6B illustrate another example of the hybrid imaging system illustrated in FIG. 1.
Figure 6B:
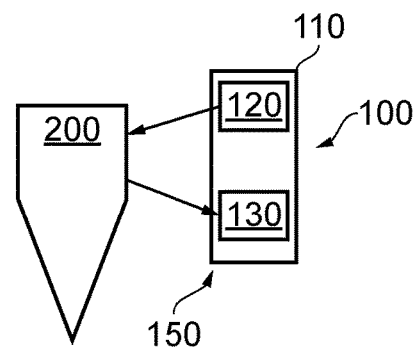

FIGS. 6A and 6B illustrate another example of the hybrid imaging system 100 illustrated in FIG. 1.

In this example, the same set of one or more light sensors 130 is used by both the lower energy light detector 150 and the x-ray detector 160.

The lower energy light detector 150 is configured to detect, using the set of light sensors 130, light from a tooth 200 illuminated by at least one of the one or more light sources 120 and the x-ray detector 160 is configured to detect, using at least the same set of light sensors 130, light from a scintillator 140 for converting externally applied x-rays to light.

The hybrid imaging system 100 therefore comprises: an intra-oral probe body 110 comprising: a lower energy light detector 150 comprising one or more light sources 120 and one or more light sensors 132 configured to detect light from a tooth 200 illuminated by the one or more light sources 120; and an x-ray detector 160 comprising a scintillator 140 for converting extra-orally applied x-rays to light for detection by the same one or more light sensors 132.

In FIG. 6A the scintillator 140 is positioned to an anterior side of the one or more light sensors 130 adjacent a posterior side 202 of the tooth 200. The scintillator 140 is positioned between the tooth 200 and the one or more light sensors 130 and obstructs x-rays passing through the tooth 200 and converts them to light travelling to the one or more light sensors 130.

In FIG. 6B, the scintillator 140 is not positioned to an anterior side of the one or more light sensors 130, so that light from a tooth illuminated by at least one of the one or more light sources 120 travels to the one or more light sensors 130 without obstruction from the scintillator 140.

A scintillator arrangement 142 may be used to control a position of the scintillator 140. In a first configuration of the scintillator arrangement 142, the scintillator 140 is positioned by the scintillator arrangement 142 at an anterior side of the one or more light sensors 130 as illustrated in FIG. 6A. In a second configuration of the scintillator arrangement 142, the scintillator 140 is either positioned away from the anterior side of the one or more light sensors 130 by the scintillator arrangement 142 or is detached from the scintillator arrangement 142 as illustrated in FIG. 6A. In the second configuration, light from a tooth 200 illuminated by at least one of the one or more light sources 120 travels to the one or more light sensors 130 without obstruction from the scintillator 140.

Referring back to FIG. 1, the intra-oral probe body 110 may comprise a detector 190 for detecting a configuration of the intra-oral probe body 110. This detector may for example detect whether the scintillator arrangement 142 is in a first configuration (e.g. FIG. 6A) or a second configuration (e.g. FIG. 6B)

The hybrid imaging system 100 may be responsive to the detector 190 detecting the first configuration of the scintillator arrangement 142 to operate as an x-ray detector 160 only and may be responsive to the detector 190 detecting the second configuration of the scintillator arrangement 142 to operate as lower energy light detector 150 only.

In at least some of the foregoing examples, the light sensors 130 described may, for example, in different implementations detect light in:
the ultraviolet (or near ultraviolet) electromagnetic spectrum only;
the infrared (or near infrared) electromagnetic spectrum only;
the visible electromagnetic spectrum only;
the ultraviolet (or near ultraviolet), the visible and the infrared (or near infrared) spectrums only;
the ultraviolet (or near ultraviolet) and visible spectrums only;
the visible and infrared (or near infrared) electromagnetic spectrums only; or
the non-ionizing electromagnetic spectrum, including visible electromagnetic spectrum, only.

Light sensors 130 may be provided by photodiodes, phototransistors, avalanche diodes, metal oxide semiconductors or any other suitable detector technology such as graphene-based detectors.

In some but not necessarily all examples, the one or more light sources 120 produce light in a first frequency band and the one or more light sensors 130 used by at least the lower energy light detector 150 detect light in a second frequency band, different to the first frequency band. This may enable fluorescent imaging.

A band-pass filter may, for example, be used to control the frequencies at which the one or more light sources 120 produce light so that, for example, at least some of the one or more light sources 120 produce light in the first frequency band but not the second frequency band.

A band-pass filter may, for example, be used to control the frequencies at which the one or more light sensors 130 detect light so that, for example, at least some of the one or more light sensors 130 detect light in the second frequency band but not the first frequency band.

In some but not necessarily all examples, the one or more light sources 120 comprise additional light sources configured to produce light in the second frequency band. This may enable optical imaging.

Where the lower energy light detector 150 is used for fluorescent imaging and also for optical imaging, they may be performed at different times to avoid interference.

The first frequency band and the second frequency band may be non-overlapping. The first frequency band may, for example, be in the ultraviolet electromagnetic spectrum or in the visible electromagnetic spectrum. The second frequency band may, for example, be in the visible electromagnetic spectrum or in the near infrared electromagnetic spectrum.

In some but not necessarily all examples, the one or more light sensors 130 are configured to detect green-blue light emitted by fluorescence of tooth enamel from ultraviolet illumination by the one or more light sources 120 (e.g. xenon light sources).

In some but not necessarily all examples, the one or more light sensors 130 are configured to detect red light emitted by fluorescence of decayed tooth enamel from ultraviolet illumination by the one or more light sources 120 (e.g. xenon light sources).

In some but not necessarily all examples, a first set of the one or more light sensors 130 are configured to detect green-blue light emitted by fluorescence of enamel from ultraviolet illumination by the one or more light sources 120 (e.g. xenon light sources) and/or a second set of the one or more light sensors 130 are configured to detect red light emitted by fluorescence of decayed tooth enamel from ultraviolet illumination. In some examples, the first and second sets are the same, in other examples, they overlap, in still other examples they are mutually exclusive.

Figure 7A:
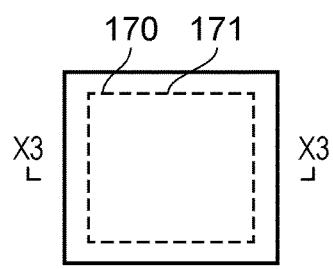
FIG. 7A illustrates a plan view of an example of an intra-oral probe body as illustrated in FIGS. 6B.
Figure 7B:
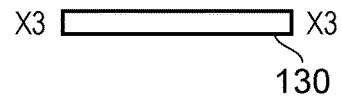
FIG. 7B illustrates a cross-section of the intra-oral probe body illustrated in FIG. 7A.

FIG. 7A illustrates a plan view of an example of an intra-oral probe body 110 as illustrated in FIG. 6B. FIG. 7B illustrates a cross-section of the intra-oral probe body 110 illustrated in FIG. 7A.

The scintillator 140 is not positioned within a perimeter 171 of the first area 170 and overlying the one or more light sensors 130.

Figure 7C:
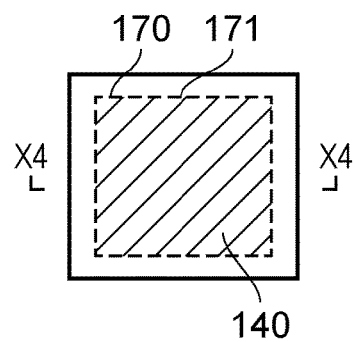
FIG. 7C illustrates a plan view of an example of an intra-oral probe body as illustrated in FIGS. 6A.
Figure 7D:
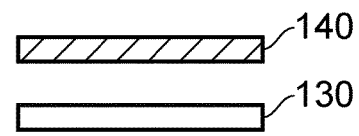
FIG. 7D illustrates a cross-section of the intra-oral probe body illustrated in FIG. 7C.

FIG. 7C illustrates a plan view of an example of an intra-oral probe body 110 as illustrated in FIGS. 6A. FIG. 7D illustrates a cross-section of the intra-oral probe body 110 illustrated in FIG. 7C.

The scintillator 140 is positioned within a perimeter 171 of the first area 170 and overlying the one or more light sensors 130.

In this example, the one or more light sensors 130 are arranged within a first area 170. In some but not necessarily all examples, the light sources 120 may be arranged around a perimeter 171 of the first area 170.

Figure 8A:
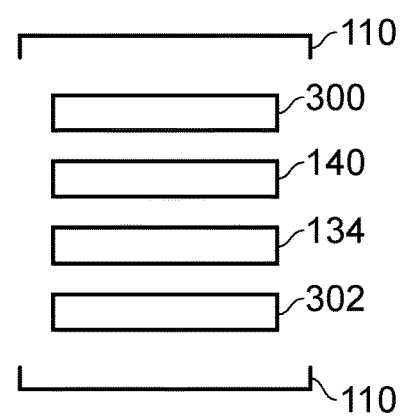
FIGS. 8A and 8B illustrate an exploded view of the same example of an intra-oral probe body from different perspective side views.
Figure 8B:
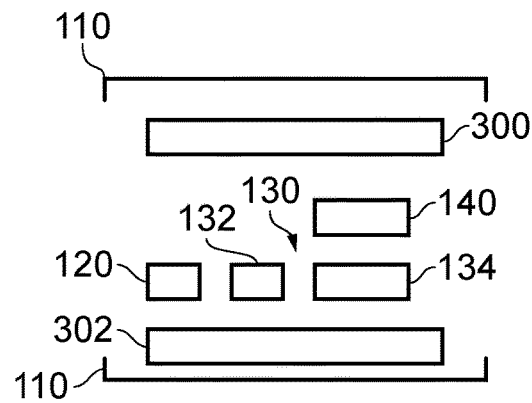

FIGS. 8A and 8B illustrate an exploded view of the same example of an intra-oral probe body 110 from different perspective side views.

The intra-oral probe body 110 is, in use, hermetically sealed.

The intra-oral probe body 110 comprises, as a stack: a shock protective layer 300; scintillator 140; light sensors 130 and light sources 120; and shared electronics 302 which may comprise a printed wiring board shared by the light sensors 130 and light sources 120.

The shared electronic circuitry 300 may for example comprise one or more of: shared signal conditioning circuitry (for amplification and/or filtering and/or analogue to digital conversion), shared power management circuitry, shared power source, shared communication interface.

In some but not necessarily all examples some or all of the shared circuitry is housed in a part of the hybrid imaging system 100 separated from the intra-oral probe body 110, such as an extra-oral body. The extra-oral body may comprise as part of the shared circuitry a shared display and/or shared user interface.

Figure 9:
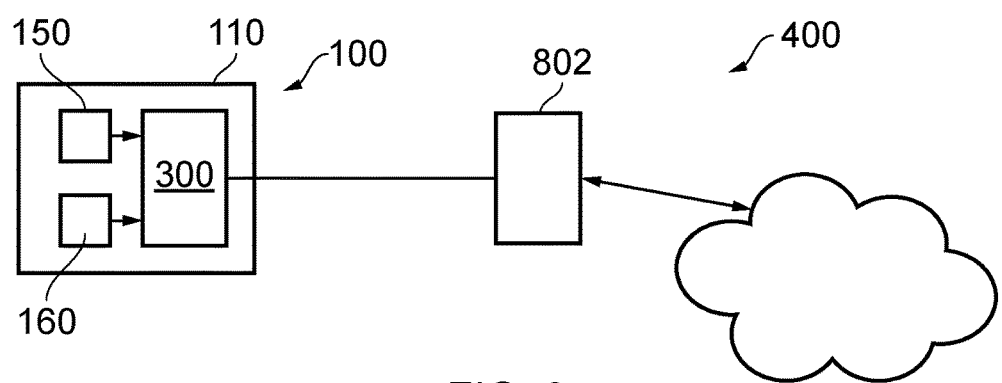
FIG. 9 illustrates an example of a system comprising the hybrid imaging system.

FIG. 9 illustrates an example of a system 400 comprising the hybrid imaging system 100. The hybrid imaging system 100 comprises the shared electronic circuitry 300, the lower energy light detector 150 and the x-ray detector 160.

In this example the system comprises a processor 402, which may be part of a local computer, for processing the sensor data recorded by the light sensors 130 of the lower energy light detector 150 and by the x-ray detector 160. The processor 402 may be configured to communicate with a remote network 404 such as the internet or 'cloud'.

In other examples, the hybrid imaging system 100 may be configured to communicate with a remote network 404 such as the internet to enable processing of the sensor data recorded by the light sensors 130 of the lower energy light detector 150 and the x-ray detector 160.

In other examples, the hybrid imaging system 100 may comprise a processor configured to process the sensor data recorded by the light sensors 130 of the lower energy light detector 150 and the x-ray detector 160.

The processing of the data recorded by the light sensors 130 of the lower energy light detector 150 and the data recorded by the light sensors 130 of the x-ray detector 160 may be processed in the same way by the same software and using the same user interface. Automatic contrast adjustment may be used to optimise the images.

Where the x-ray detector 160 and the lower energy light detector 150 take images of the same tooth from different perspectives, the images may be combined to form a composite image.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed. For example, although the preceding description describes imaging of an object using a probe in the specific context of imaging a tooth using an intra-oral probe, the invention has broader application and may be used in other medical and industrial applications.

In general a probe body comprising: one or more light sources; one or more light sensors; an x-ray detector configured to detect, using at least one of the one or more light sensors, light from a scintillator for converting extra-orally applied x-rays to light; and a lower energy light detector configured to detect, using at least one of the one or more light sensors, light from an object illuminated by at least one of the one or more light sources., may be used. An example of a non-medical, industrial application is imaging a welding joint to determine the quality of the weld.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A probe body configured to be placed intra-orally, the probe body comprising:
one or more lower energy light sources;
two or more lower energy light sensors comprising at least a first lower energy light sensor and one or more different second lower energy light sensors;
a light detector configured to detect, using at least the first lower energy light sensor, light from an object illuminated by at least one of the one or more lower energy light sources; and
an x-ray detector configured to detect, using at least one of the one or more different second lower energy light sensors, light from a scintillator for converting extra-orally applied x-rays to lower energy light,
wherein lower energy light is light that has a lower energy than an x-ray wavelength light on an electromagnetic spectrum.

2. The probe body of claim 1, wherein the probe body is configured to flex and/or is configured to bend and/or is configured to contort.

3. The probe body of claim 1, wherein the one or more different second lower energy light sensors are arranged within a first sub-area of a first area and the first lower energy light sensor is arranged within a second sub-area of the first area, wherein the first sub area and the second sub-area do not overlap, the probe body comprising a scintillator positioned within a perimeter of the first area and overlying the first sub-area but not the second sub-area.

4. The probe body of claim 1, wherein the probe body comprises at least a first part and a second part, wherein the first part houses the light detector comprising the first lower energy light sensor and the one or more lower energy light sources and the second part houses the x-ray detector comprising a scintillator and the one or more different second lower energy light sensors.

5. The probe body of claim 4, wherein the probe body comprises a third part, wherein the third part houses a further light detector comprising two or more lower energy light sensors and one or more, lower energy light sources, wherein the second part lies between the first and third part.

6. The probe body of claim 4, wherein the object is a tooth, and wherein the first part is movable relative to the second part such that the first part is adjacent a top surface of the tooth and the second part is adjacent a posterior surface of the same tooth but not the top surface of the tooth.

7. The probe body of claim 1, wherein the light detector is configured to detect, using at least a first set of one or more lower energy light sensors, light from an object illuminated by at least one of the one or more lower energy light sources and wherein the x-ray detector is configured to detect, using at least the first set of the one or more lower energy light sensors, light from a scintillator for converting externally applied x-rays to light.

8. The probe body of claim 7, comprising a scintillator arrangement, the probe having a first configuration in which a scintillator is positioned by the scintillator arrangement to an anterior side of the first set of one or more lower energy light sensors, so that externally applied x-rays are converted to lower energy light that travels to the first set of one or more lower energy light sensors; and a second configuration in which a scintillator is not positioned by the scintillator arrangement to an anterior side of the first set of one or more lower energy light sensors, so that lower energy light from an object illuminated by at least the one or more lower energy light sources travels to the first set of one or more lower energy light sensors without obstruction from the scintillator.

9. The probe body of claim 1, wherein the probe body comprises a detector for detecting a configuration of the probe body.

10. The probe body of claim 1, wherein the two or more lower energy light sensors detect light in the visible electromagnetic spectrum and/or in the infrared electromagnetic spectrum.

11. The probe body of claim 1, wherein the one or more lower energy light sources produce lower energy light in a first frequency band; and wherein the two or more lower energy light sensors detect light in a second frequency band, different to the first frequency band.

12. The probe body of claim 1, wherein the one or more lower energy light sources are arranged around a perimeter of a first area comprising the two or more lower energy light sensors.

13. The probe body of claim 1, wherein the x-ray detector and the light detector use shared electronic circuitry.

14. The hybrid imaging system comprising the probe body of claim 1 and a computer system located either locally or remotely from the probe body.

15. A probe body configured to be placed intra-orally, the probe body comprising:
one or more lower energy light sources;
two or more lower energy light sensors comprising at least a first lower energy light sensor and one or more different second lower energy light sensors;
a light detector configured to detect, intra-orally, using at least the first lower energy light sensor, light from an object illuminated intra-orally by at least one of the one or more lower energy light sources
wherein the probe body is configured to flex or bend or contort or any combination thereof; and
an x-ray detector configured to detect, using at least one of the one or more different second lower energy light sensors, light from a scintillator for converting extra-orally applied x-rays to lower energy light,
wherein lower energy light is light that has a lower energy than an x-ray wavelength light on an electromagnetic spectrum.

16. The probe body of claim 15, wherein the one or more lower energy light sources produce lower energy light in a first frequency band; and wherein the two or more lower energy light sensors detect lower energy light in a second frequency band, different to the first frequency band, wherein the two or more lower energy light sensors detect light in the visible electromagnetic spectrum and/or in the infrared electromagnetic spectrum.

17. The probe body of claim 15, wherein the lower energy light sources are arranged around a perimeter of a first area comprising the two or more lower energy light sensors.

18. The probe body of claim 15, wherein the x-ray detector and the light detector use shared electronic circuitry.

19. The probe body of claim 15, wherein the one or more lower energy light sources produce lower energy light in a first frequency band; and wherein the two or more lower energy light sensors detect lower energy light in a second frequency band, different from the first frequency band, wherein the two or more lower energy light sensors detect lower energy light in the visible electromagnetic spectrum and/or in the infrared electromagnetic spectrum, wherein the one or more lower energy light sources are arranged around a perimeter of a first area comprising the two or more lower energy light sensors, and wherein the x-ray detector and the light detector use shared electronic circuitry.

* * * * *